Figure 1:
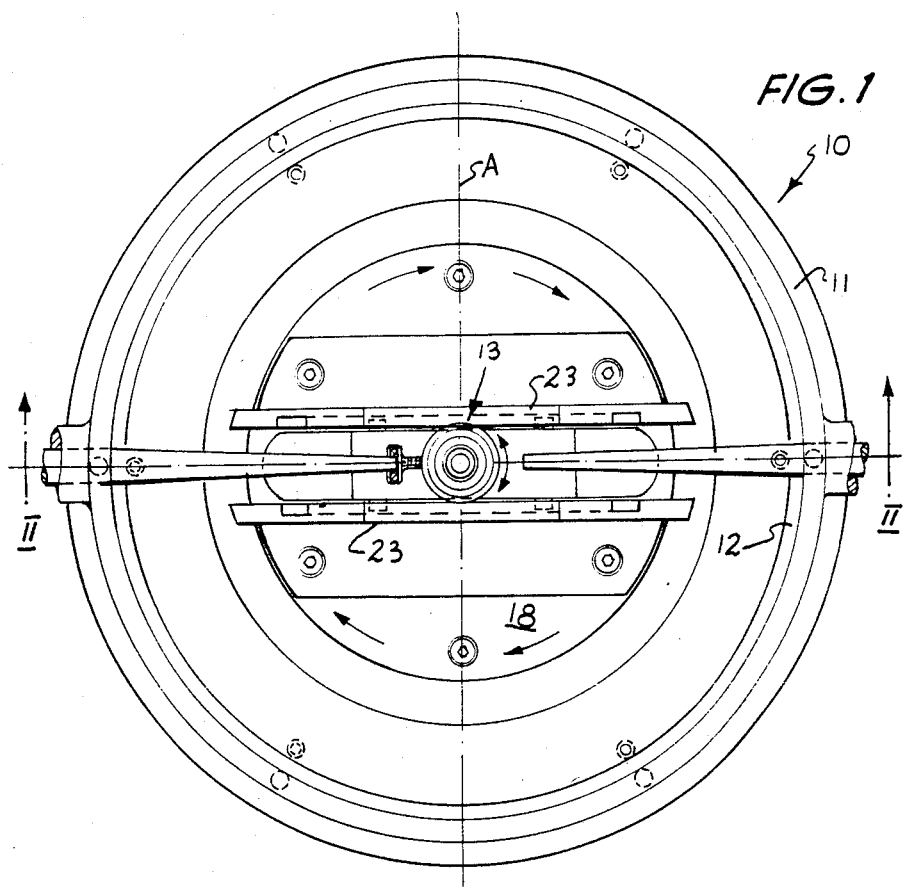

United States Patent [19]

Manners

[11] Patent Number: 4,573,182
[45] Date of Patent: Feb. 25, 1986

[54] X-RAY DIFFRACTION CAMERA

[76] Inventor: Vincent J. Manners, 29 Mepunga St., Concord West, New South Wales, Australia, 2138

[21] Appl. No.: 595,998

[22] Filed: Mar. 28, 1984

[30] Foreign Application Priority Data

Mar. 29, 1983 [AU] Australia .................. PF8662

[51] Int. Cl.$^4$ .................. G01N 23/205; G01N 23/207
[52] U.S. Cl. .................. 378/075; 378/81
[58] Field of Search .................. 378/73, 75, 77, 79, 378/81

[56] References Cited

U.S. PATENT DOCUMENTS 2,317,329  4/1943  McLachlan .................. 378/75
4,413,354 11/1983  Manners .................. 378/75

FOREIGN PATENT DOCUMENTS 0034035  8/1981  European Pat. Off. .................. 378/79

Primary Examiner—Alfred E. Smith
Assistant Examiner—T. N. Grigsby
Attorney, Agent, or Firm—Merchant, Gould, Smith, Edell, Welter & Schmidt

[57] ABSTRACT

An X-ray diffraction camera which rotates a sample about two generally normal axes while simultaneously rotating the sample about a third axis which changes in angular relationship relative to the two normal axes, said camera further providing linear reciprocation of the sample along said third axis.

8 Claims, 3 Drawing Figures

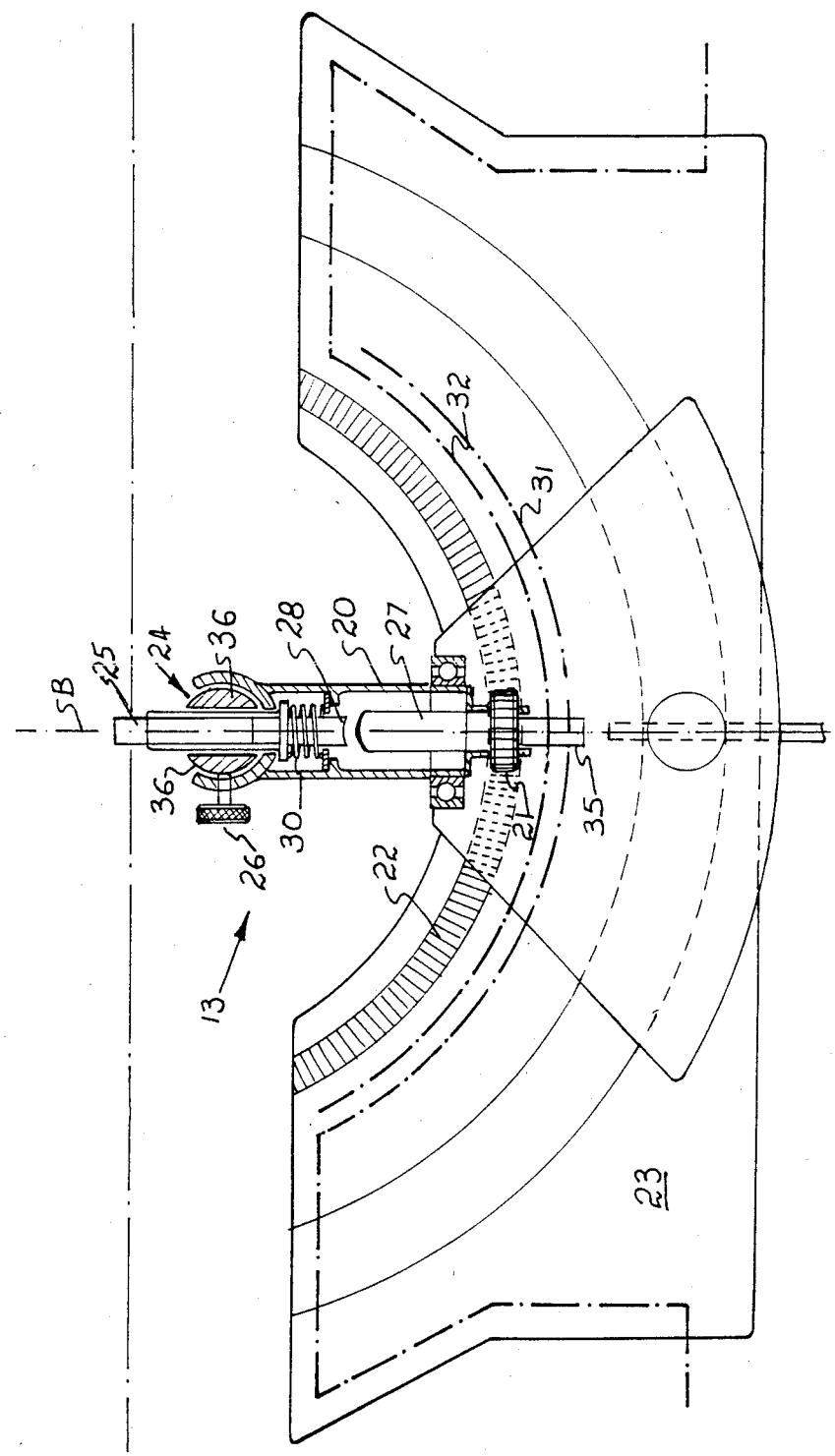

X-RAY DIFFRACTION CAMERA

The present invention relates to cameras for X-ray diffraction analysis of crystalline samples to determine, for example, unit cell geometry, unit cell size, and crystalline structure (arrangement of atoms within the unit cell). The present invention also relates to X-ray goniometers.

Known cameras utilise an X-ray collinating system which directs a narrow beam of X-radiation at a specimen which results in the recording on a film of an X-ray diffraction pattern of the specimen.

One particular system is known as the powder diffraction technique. Similar techniques are described in U.S. Pat. Nos. 3,189,741; 3,944,823; 3,509,336; 3,631,240; 3,566,112; 3,189,741; 3,564,240; 3,714,426; and 3,728,541.

The essential feature of the powder diffraction technique is that a narrow beam of monochromatic X-rays impinge upon a crystalline powder composed of fine randomly oriented particles—ideally, all possible orientations of all possible lattice planes are present so that the X-ray beam will always find some crystallites of the proper orientation to fulfill the Bragg condition for reflection. In practice, to ensure the existence of a sufficient number of the required orientations to give a usable film from a Debye Scherrer camera, it is usually necessary to rotate, oscillate or otherwise move very small samples continuously during the X-ray exposure. However a single crystal; i.e., one whose lattice planes are all fixed in respect to any chosen edge of the crystal cannot give a complete powder pattern as only a very few of its lattice planes will be in a position to reflect the X-rays according to the Bragg law and hence the X-ray picture will consist of a number of spots apparently randomly oriented. There is a definite need for an instrument that will yield X-ray diffraction patterns useful for identification purposes from larger single crystals, coarse crystalline aggregates, fibres or very small samples and preferably the powder-type patterns because there is so much information available in powder diffraction data files.

Until recently powder patterns were normally restricted to the determination of the unit cell dimensions and their geometry. To determine the arrangement of atoms within the unit cell a variety of single crystal techniques were used. In principle, however, a powder pattern contains the same information as a single crystal pattern. Because of the finite resolution of the collinating system the powder pattern actually consists of a set of overlapping lines and up till the discovery by Rietveld in 1969 of profile analysis it was thought that the individual powder line intensities could not be separated into their respective components. With this new development it has become possible to use the powder diffraction technique for structure determinations provided that there was freedom from preferred orientation in the powder pattern. It is a basic assumption of profile analysis that the reflected intensity of each individual reciprocal lattice point is spread uniformly over the surface of a sphere.

While the prime purpose for the development of the camera under discussion has been to produce a unit which will eliminate preferred orientation effects in single crystals or fibres, the discovery of profile analysis has greatly enhanced the range of its usefulness in that it can be used for a number of types of X-ray diffraction analyses now requiring special cameras.

A number of attempts have been made to produce such a camera, but all have their limitations; e.g., Switzer and Holmes (Amer. Miner 32, 1947), produced a camera which gave only some of the back reflection lines on a rotating film holder. J. Gracker and D. A. Helinek (Norelco Reporter XIII (3) 1966) used the normal Debye-Scherrer camera and by means of an airstream, levitated and spun a sample, which had been ground into a spherical shape, in the X-ray beam. G. Gandolfi (Miner. Petrogr. Acta, 13 pp 67-74) used a Debye Scherrer camera which contained two sample holders, the first of which was inclined at 45° to the vertical axis, after the initial exposure was made in this fashion. The sample was then transferred to a vertical sample holder and a second exposure made using the normal Debye Scherrer technique. Unless the sample is placed precisely concentric with the original sample, variations can occur in both the position and intensity of the diffraction lines. Moreover the instrument will not record a complete powder diagram for a triclinic crystal and hence will not provide a random sample of reciprocal space.

It has been pointed out that a major requirement for success with the powder pattern technique is freedom from preferred orientation effects in the specimen. This can be achieved in two ways. The first is by the careful preparation of the sample which among other things requires the reduction of the size of crystallites to between 10 m and 0.1 m and then randomly packing them into a fine sample holder. This can be extremely difficult especially with needle-like or plate like crystallites. The second method is to mechanically move any form of specimen so that each grain takes up all possible orientations with equal probability. This technique has had only a low success rate because of the difficulty of producing random motion.

By definition random motion postulates that such motion be completely unpredictable in the time domain. From this it must be concluded that with respect to the X-ray beam there should be the same probability that every possible orientation of the crystal planes will occur with equal likelihood in a sample undergoing random motion. As far as random motion is concerned its instantaneous vector can be described in terms of motion about the three co ordinate axes together with motion along those axes. In order therefore to generate random motion all of these motions should be available to the sample. Again ideally there should be no pattern of recurrences. In practice this is virtually impossible to achieve in any mechanical system.

In U.S. Pat. No 4,413,354, there is described an X-ray diffraction camera having a hypocycloidal gear train adapted to cause rotation of the sample within the camera about two generally normal axes. The present invention, although not restricted to use with this camera, is particularly useful when adapted for operation with this camera. More particularly, U.S. Pat. No. 4,413,354 attempts to approximate random motion of the sample by approximating random rotation about two generally normal axes. The camera of this U.S. patent however lacks any random motion which can be attributed to linear motion of the sample.

It is the object of the present invention to overcome or substantially ameliorate the abovementioned disadvantages.

There is disclosed herein an X-ray diffraction camera having a sample support to position the sample at a predetermined location, means to receive and support a film, means to direct X-rays at the sample so that scattered rays leaving said sample expose said film, and drive means to cause motion of said sample support so that movement of said sample approximates random motion, said drive means being adapted to rotate said sample support about at least one axis and to move said sample linearly intermittently during rotation of said sample.

Figure 2:
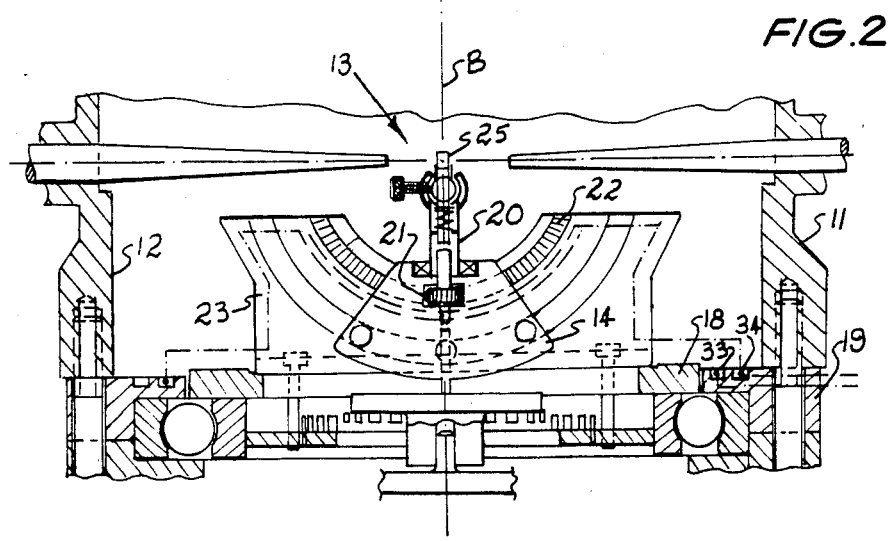

A preferred form of the present invention will now be described by way of example with reference to the accompanying drawings wherein:

FIG. 1 is a schematic plan view of an X-ray camera;
FIG. 2 is a schematic side elevation of a portion of the camera of FIG. 1; and
FIG. 3 is a schematic enlarged view of a portion of the camera of FIG. 1.

In FIGS. 1 to 3 there is schematically depicted an X-ray diffraction camera 10. The camera 10 is substantially identical in construction to the camera of U.S. Pat. No. 4,413,354 except that the sample holder 13 which receives a crystalline sample is subjected to additional rotation with linear motion being super-imposed upon the rotational movement of the sample. The camera 10 includes a cylindrical housing 11 having an internal surface 12 which receives a strip of film so that the film forms the configuration of a cylinder. Located centrally of the housing 11 is a sample holder 13 which receives the crystalline sample to be subjected to a narrow beam of monochromatic X-rays with the result that the X-rays will be scattered by refracting planes of the sample. The scattered rays impinge on the film. The sample holder 13 is mounted on a sample support 14 which is movably mounted on a base 18. The base 18 is rotatably supported on a main frame 19. Operation of the camera 10 is basically as described in U.S. Pat. No. 4,413,354 in that the sample holder 13 is rotated about the two axes A and B.

In the present instance random motion of the sample is more closely approximated by rotating the sample holder 13 about a third axis which is the axis of a shaft 20 supporting the holder 13. The shaft 20 is caused to oscillate about the axis A in accordance with movement of the sample support 14. However, the shaft 20 is rotatably supported by the sample 14 and includes a pinion gear 21 fixed to the shaft 20. The pinion gear 21 is adapted to engage a rack 22 formed on one of the support plates 23 forming part of the base 18.

As the sample support 14 is moved through 90° about the axis A and is rotated about the axis B, the rotational direction of the sample holder 13 about the axis of the shaft changes in direction.

It should be appreciated that only one of the support plates 23 is provided with a rack 22 while the pinion gear 21 would be clear of movement from the other plate 23.

Now with particular reference to FIG. 3, wherein the sample holder 13 is more fully depicted.

The sample holder 13 includes an adjustable guide assembly 24 including guide plates 36 and threaded adjustment member 26 which are adjustable so as to secure the sample 25 in position while allowing linear movement thereof along the axis of the shaft 20. Mounted within the shaft 20 is a solenoid 27 which causes linear reciprocation of a metal pin 28 to which a sample 25 is secured. The pin 28 has a flange 29 against which the spring 30 bears to bias the pin 28 to the position depicted. The solenoid 27 receives intermittent DC current from two strips of conductor 31 and 32 which in turn receive electric power from lines 33 and 34 fixed to the base 19. Contact of the conductors 31 and 32 with the lines 33 and 34 is achieved by brushes. Additionally the solenoid would be provided with brushes 35 which contact the conductors 31 and 32. The solenoid 27 would be mounted concentric of the shaft 20 and would pass through the centre of the pinion gear 21. To provide intermittent linear motion of the pin 28, and therefore the sample 25, the conductors 31 and 32 would have intermittent patches which would deactivate the solenoid 27. As the support 14 is caused to rotate about the axis A, the brushes 35 would pass along the conductors 31 and 32 thereby engaging the conductive portions exposed of the conductors 31 and 32 to thus cause intermittent actuation of the solenoid 27.

The abovedescribed preferred embodiment provides the motion required to achieve randomness in respect of motion of the sample 25. To achieve the maximum delay between coincidences relatively prime number gear ratios are used in all the drive mechanisms which control the motion about the three co-ordinated axes. Added to this the sample is vibrated along the instantaneous axis of rotation of the shaft 20 by intermittent actuation of the solenoid 27. Additionally the abovedescribed preferred form of the present invention introduces an extra rotational movement to the sample which rotational movement changes in direction. In this way motion of the sample more closely approximates random motion with respect to the X-ray beam.

It should further be appreciated that in the present form of the invention, the drive mechanism is described in U.S. Pat. No. 4,413,354. However other drive mechanisms are within the scope of the present invention provided rotation of the sample about at least one axis is achieved.

What I claim is:

1. An X-ray diffraction camera having a sample support to position the sample at a predetermined location, means to receive and support a film, means to direct X-rays at the sample so that scattered rays leaving said sample expose said film, and drive means to cause motion of said sample support so that movement of said sample approximates random motion, said drive means being adapted to rotate said sample support about at least one axis and to move said sample linearly intermittently during rotation of said sample.

2. The camera of claim 1 wherein said drive means rotates said sample about two normal axes intersecting at said predetermined location.

3. The camera of claim 2 wherein said drive means rotates said sample about a third axis which changes in angular relationship relative to said two normal axes, with said third axis also intersecting the other axes at said predetermined location.

4. The camera of claim 3 wherein said drive means reciprocates said sample linearly of said third axis.

5. The camera of claim 1 wherein said drive means comprises a base rotatable about a first axis, a sample mounting mounted on said base so as to be rotated about a second axis normal to said first axis and intersecting therewith at said predetermined location, said sample support being mounted on said sample mounting for rotation about a third axis intersecting with the other axes at said predetermined location and rotating with said sample mounting so that the relative angular position of said third axis relative to said two normal axes changes.

6. The camera of claim 5 wherein said sample is linearly reciprocated along said third axis.

7. The camera of claim 6 wherein rotation about said third axis is achieved by a rack and pinion mounted on said sample mounting.

8. The camera of claim 7 wherein linear movement of said sample support is achieved by an intermittently operated solenoid mounted on said sample support.

* * * * *